United States Patent [19]

Ibing et al.

[11] 4,036,594
[45] July 19, 1977

[54] APPARATUS FOR RECOVERING HIGHER MELTING ORGANIC MATERIALS VIA FRACTIONAL SUBLIMATION

[75] Inventors: Gunter Ibing, Mulheim (Ruhr); Herbert Haferkorn, Bottrop, both of Germany

[73] Assignee: Veba-Chemie AG, Gelsenkirchen-Buer, Germany

[21] Appl. No.: 596,349

[22] Filed: July 16, 1975

Related U.S. Application Data

[62] Division of Ser. No. 533,416, Dec. 16, 1974.

[30] Foreign Application Priority Data

Dec. 17, 1973 Germany .............................. 2362659

[51] Int. Cl.² .......................................... B01D 7/02
[52] U.S. Cl. ..................................... 23/264; 23/293 A;
23/294 R; 23/273 R; 260/346.3; 260/346.7;
260/706; 165/94; 159/6 W; 55/82; 202/185 R;
202/185 E

[58] Field of Search ............ 23/294, 293, 264, 273 R;
260/346.3, 346.7, 706; 165/94, 161, 164, 61;
159/6 W; 55/82; 202/185 R, 185 E;
210/184–186

[56] References Cited

U.S. PATENT DOCUMENTS

| | | | |
|---|---|---|---|
| 1,023,402 | 4/1912 | Whiting | 165/161 |
| 2,112,024 | 3/1938 | Jarl et al. | 23/264 X |
| 2,692,657 | 10/1954 | Barton | 55/82 |
| 3,079,993 | 3/1963 | Sweet | 23/264 X |
| 3,289,838 | 12/1966 | Garrett | 210/186 X |
| 3,609,943 | 10/1971 | Richter | 55/82 |

*Primary Examiner*—James H. Tayman, Jr.
*Attorney, Agent, or Firm*—Burgess, Dinklage & Sprung

[57] ABSTRACT

An apparatus for recovering higher melting organic materials which is an upright column containing a gas inlet at a lower portion thereof and a gas outlet at the upper portion thereof. The apparatus has a wall disposed in the flow of the gas between the gas inlet and the gas outlet which wall is perforated to allow gas to flow therethrough. Cooling means are provided on the side of the wall away from the gas inlet to cool components of a gas flowing therethrough.

7 Claims, 6 Drawing Figures

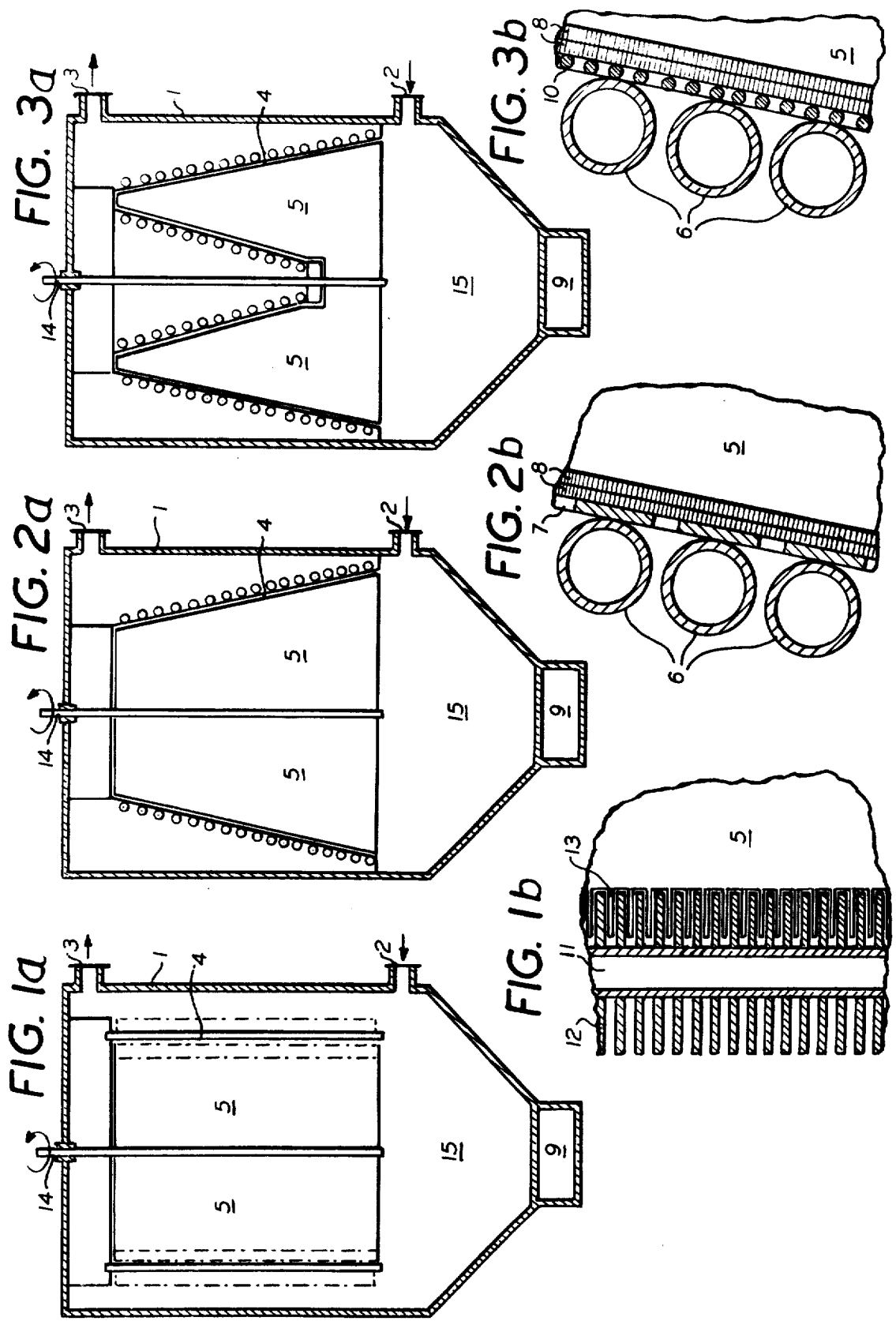

APPARATUS FOR RECOVERING HIGHER MELTING ORGANIC MATERIALS VIA FRACTIONAL SUBLIMATION

This is a division, of application Ser. No. 533,416 filed Dec. 16, 1976.

BACKGROUND OF THE INVENTION

The commercial recovery of particularly pure, sublimable, organic materials, i.e. such materials which under the working conditions pass over immediately from the gaseous state into the solid state, from a hot gas mixture, which is mainly taken from a reactor for the production of said materials, and which contains as impurities side products which, under the required working conditions, remain in gaseous form in the exhaust gas, has gained in importance in recent years.

The separation of the sublimable materials from these gas mixtures containing them is known. All known methods have in common that the hot gases must be cooled off to such a degree on cooled surfaces that the desired separation degree for the substance to be obtained is achieved. In this connection, the heat exchange surfaces often get coated with products so that a periodic removal is necessary. Large sublimation chambers can easily be emptied with scrapers or brushes. However, due to the relatively small chamber surfaces, the throughput or area-time-yield is low. The most economical separators at the present time are ribbed pipe condensers which, however, cannot be emptied mechanically. The recovery of the sublimate or condensate takes place here by periodic heating up of the ribbed pipes to temperatures above the hardening point of the products recovered and the withdrawal of the melt into storage bins. The disadvantage in this method consists in the requirement of two condensers which have to be operated alternately, of which one is being loaded while the other is melted off. Furthermore, such a condenser is unsuitable for products which have a very high melting point and/or which disintegrate at their melting point.

Pyromellite acid dianhydride (PMDA), among others, belongs to the products which cannot be obtained in the ribbed pipe condenser of the customary construction. On the one hand, the melting point of 285° C is so high that the melting off would create technical difficulties, on the other hand, a discoloration of the product appears when the PMDA is heated to its melting temperature, which cannot be neutralized according to hitherto known methods except through distillation, which due to the high melting point of the product creates technical problems which are also not negligible.

DISCUSSION OF THE PRIOR ART

Various methods are known in the literature for the separation of PMDA from the reaction gases:

The use of sublimation chambers has been suggested repeatedly whereby baffle plates can be built in to improve the effectiveness of these cooling surfaces, or a cooling off of the gases can be effected by injecting water, whereby the cooling however may not exceed 555° C/sec. A disadvantage in this latter method is the increase of the condensation point for water, which results in an increased formation of pyromellite acid (PMA). More favorable appears to be the mixing of the hot reaction gases with cold air. However, in this connection very fine crystals develop which due to the increase of the velocity of flow are carried away from the sublimation chamber in increasing amounts. Filter- or water washes have been suggested for avoiding such losses.

Considerably easier is the water wash of the entire reaction gases. Thereby, the entire product results in PMA which then again must be dehydrated to dianhydride by various methods.

With another method, the hot PMDA-containing reaction gases are brought in contact with pneumatically transported solid balls which in turn absorb the heat and at the same time coat themselves with sublimating substance. In a separate installation, the solid balls are mechanically (baffle effect) cleaned and cooled, prior to being returned again to the sublimation chamber. This method, understandably, requires a complicated apparatus.

It is furthermore known that the PMDA resulting from the gas phase oxidation of tetra-alkylated benzenes (e.g. dural) is contaminated with a number of side products, the vapor pressures of which are higher than the pressure of the PMDA and/or because of their higher dilution in the reaction gas have a lower condensation point. To this group belong, among other, trimellite acid anhydride, dimethylmonomethyl phthalic acid anhydride and phthalic acid anhydride as a colorless impurity, aside from a number of other darkly colored compounds. Refining is necessary for the removal of these impurities. The proposed methods usually deal with solvents as a treatment of the crude product, particularly ketones or solvent mixtures, while another method became known according to which a hot inert gas or air is passed over or through the crude product at temperatures between 100° and 200° C in amounts of 1 to 150 kg gas/kg crude PMDA, until a purity degree equal to 99% is reached.

It is also known that pure PMDA can be obtained if the sublimation of the crude product is carried out at temperatures between 130 and 200° C.

SUMMARY

It has now surprisingly been discovered that particularly pure products can be obtained if the method for the recovery of higher melting, organic substances, whose crystals exhibit a distinct heat conductivity, is carried out in such a manner through fractionated sublimation of a carrier gas stream which contains these substances and impurities in vapor form by cooling off to a temperature at which the desired separation degree is reached and/or the undesirable impurities remain still in gaseous form in the carrier gas stream, that first:

a. the gas stream is precooled in a known manner to a temperature above the saturation point, preferably 5°-10° C, if necessary diluting the gas stream with air or inert gas that said temperature is distinctly below the melting point of the sublimate, and subsequently b. the precooled gas stream is passed through a cooling layer which is thermostatically adjusted to a temperature above the condensation point of the impurities, however below the saturation temperature for the product to be obtained, and the separated crystals are removed from the cooling surface with a scraping device.

Sets of ribbed pipes placed side by side have proved suitable as thermostatically controlled, perforated cooling layer. Thus, it has surprisingly been discovered that, when introducing a reaction gas containing about 7 grams of PMDA/Nm³ from an oxidation furnace, after precooling to 220° C, into a ribbed pipe condenser, which was thermostatically adjusted with a cooling oil to a temperature of 130° C, particularly pure PMDA sublimated which only accumulated at the edges of the cooling ribs of the first ribbed pipe of the set facing the gas stream, whereby the crystals grew against the gas stream. Between the cooling ribs on the other hand, no crystallization could be detected. The entire cooling rib set was free and only past it, when the gas was further cooled off, a darkly colored product resulted which contained only little PMDA.

Also suitable are cooling layers consisting of one or more perforated sheets, to the back side of which cooling pipes are affixed. The same observation was made when an identical hot reaction as containing PMDA with a temperature of 220° C was passed vertically through a perforated sheet (5mm perforation-diameter; ca. 60% free throughpassage), which was thermostatically adjusted to 130° C with the aid of cooling pipes soldered on to the side facing away from the gas stream. On the leading edge of the perforated sheet, pure PMDA crystals grew, while only small amounts of heavily contaminated products precipitated from the exhaust gas.

Instead of the perforated sheets, also narrowmeshed wire netting may be used, to the back side of which cooling pipes are also affixed. The same resulted when the perforated sheet was replaced by a wire meshing (4-5mm mesh width, 0.8 wire thickness). Hereby, the heat transfer between cooling copper pipe and the wire mesh (high quality steel) took place through loose contact.

Aside from these exemplified cooling layers also similar ones according to the invention can be used.

This observation is explained by the assumption of an increase of a distinct heat conductivity by the growing crystals. Through only a slight cooling off by a few degrees C below the condensation point for PMDA, which in the case of the reaction gases used was about 200° C, a considerable portion of the PMDA precipitates, which then settles on the cool metal surface in the form of fine needles. These fine crystals now have a considerable surface area on which the freshly onflowing hot gas can cool off prior to even reaching the metal surface. The PMDA which separates thereby, settles on the already present crystal, which thus grows in length and thickness. The lengthwise growth is opposite to the gas flow. According to the heat conduction in the crystal, the growth in thickness will be heavier at the base of the crystal, the higher the flow velocity of the gas is. In this connection it is essential that the temperature of the onflowing gas is lower than the melting point of the crystal, as otherwise a decrease of the crystal surface results through the melting together. These considerations were confirmed by experiments which were carried out.

This method is thus particularly suitable for such higher melting, organic substances whose crystals have a distinct heat conductivity. As such may be named particularly the polycarboxylic acid anhydrides, which can be obtained through gas phase oxidation over fixed bed- or fluidized bed catalysts. The method according to the invention is demonstrated in the example of the pyromellite acid dianhydride. But also aromatic nitriles can be obtained in this manner.

If a provision is made to periodically remove the accumulated crystals mechanically from the contact surface, then the apparatus for the sublimation can be operated continuously.

DESCRIPTION OF THE DRAWINGS

FIGS. 1a-3b show three different types of equipment of possible devices for the carrying out of the method according to the present invention for the recovery of higher melting, organic substances.

The b- figures show detailed portions of the devices of FIGS. 1a, 2a and 3a.

FIG. 1a shows the upright standing container 1 with a gas entrance connection 2 which is affixed to the lower lateral portion, and a gas exit connection 3 in the upper portion of the container. The thermostatically controlled, perforated cooling layer 4 is located between the gas entrance and gas exit connection, which encloses a cylindrical oncoming flow area. On the leading edge there is a collection device 5 which, for example, can be shaped comb-like 13 or which may have a brush 8. The collection device 5 is turned periodically or continually via a shaft 14 whereby the type of rotation is dependent on the amount of the separated crystals and their characteristics. The periodic collection is preferred in the case of small amounts per time unit. The bottom part 15 of the container 1 is for practical purposes tapered and has a device for the removal of the product 9.

The detail A shows FIG. 1b. A set of ribbed pages 11 with the cooling ribs 12 is arranged parallel to the lateral container wall. The teeth 13 of the comb which is attached to the vertical edges of the rotating tin blade 5 interlock into the cooling ribs 12 on the onflowing side. The cooling medium, which is supposed to keep the perforated cooling layer at an even temperature as much as possible, is guided through the ribbed pipe 11. In order to achieve this, one works with relatively high flow velocities. This makes it possible to keep the temperature of the cooling layer constant and to remove the crystallization heat.

FIG. 2a shows a different embodiment of the onflow area which has the shape of a hollow truncated cone which is open at the bottom. The other elements of the device correspond to those of FIG. 1a. The detail B shows a perforated sheet 7 with soldered-on cooling pipes 6 at the side facing away from the onflow side for the collection of the cooling medium. The collection device 5 carries brushes 8 for removal of the product from the perforated sheet 7.

FIG. 3a corresponds in principle with FIG. 2a with the exception of the construction of the lead-in area, which has the shape of a hollow bulge which is open at the bottom with triangular cross-section, and the element evident from the detail. Instead of the perforated sheet 7 of FIG. 2b, FIG. 3b shows a wire mesh 10.

Aside from the collection device and the comb and brushes as described, of course, wiper blades can also be used. The removed crystals then reach the tapered lower portion 15 of the container 1, from where they can be removed via a corresponding device 9.

There are also other possibilities aside from the cross-sections of the flow area illustrated in the figures. For instance, the cooling layer may have the shape of a half hollow sphere or paraboloids. Also hollow cones or pyramidal shapes are feasible. Also hollow bulges which are open at the bottom are suitable with the aforementioned cross-section shapes.

Cooling layers in the shape of hollow cylinders are also suitable for carrying out this method. In these cases, the open bottom area must be facing the flow side.

Generally speaking, any horizontal or inclined plane area position can be used as thermostatically adjusted perforated cooling layer.

The nature of the invention is illustrated in the following examples:

EXAMPLE 1

A ribbed pipe set of 4 parallel arranged ribbed pipes, 350 mm long, whose square ribs with an edge length of 30 mm at a distance of 5 mm are arranged in such a manner that all the lower ribbed edges were all in one plane, was installed into a rectangular shaft with a cross-section of 140 × 350 mm and was thermostatically adjusted to 145° C. Through this arrangement was passed a reaction gas stream of 3.260 $Nm^3/h$, which contained 4.32 g $PMDA/Nm^3$ in the form of vapor and was precooled to 220° C. During an operating period of 118 hours, 1.600 gram PMDA sublimated with a purity of 99.93% in such a manner at the cooling ribs that over the entire area below the cooling ribs a dense network of prismatic crystals developed which were 3–4 cm. long and up to 10 mm thick. The crystals were attached relatively loosely to the edges of the cooling ribs facing the gas flow. The surfaces of the cooling ribs and the pipes were absolutely clear. Beyond the ribbed pipe set, 137 gram of darkly colored crystals could be recovered through further cooling, which contained only 36% by weight PMDA. The sublimation at the cooler thus amounted to 96% of theory.

EXAMPLE 2

A wire mesh (1.0 mm wire thickness, high grade steel, 4.5 mm loose mesh width) with an edge length of 400 × 250 mm was rolled up into a cylinder with a diameter of 12 mm and a height of 250 mm was enclosed by a fitting basket made of copper pipes, which could be fed by a thermostat, and supplied with a cover which could be guided up and down along the cylinder axis. This cooling basket was placed in such a manner into a heated pipe with a diameter of 400 which was subdivided by an apertured partition, that a hot reaction gas introduced at the lower portion of this pipe could only reach the upper part of this pipe if it passed the inserted cooling basked from the inside to the outside.

This apparatus was fed with 1.390 $Nm^3$ of reaction gas/h, which was precooled to 220° C. The cooling basket was thermostatically adjusted to 140° C. The exiting gases had a temperature of 150° C. Every 24 hours, the cover of the cooling basket was once guided from top to bottom and back, whereby the crystals accumulated on the inside of the cooling basket were thrown into the lower part of the pipe which was heated to 200° C. After 10 days of operation the test was terminated. The cooling basket was completely clean on the inside. Outside the basket there were very few discolored crystals on the cooling coils. The product resulting in the lower end of the pipe, which amounted to 84.2% of the entire sublimate, had a purity of 99.94%. In subsequently added sublimators, 15.8% sublimate with only 32.84% by weight PMDA were recovered. The net PMDA result was 94% of theory.

EXAMPLE 3

Instead of the wire mesh of Example 2, a perforated sheet (5mm borehole, about 50% free passage) was installed in the otherwise identical apparatus. A rotating steel brush was affixed for periodic cleaning of the inner perforated sheet surface. The sublimator was fed with 1.900 $Nm^3$ of reaction gas/h precooled to 220° C from a PMDA testing oven. The cooling basket was thermostatically adjusted at 130° C. The exiting remaining gases showed a temperature of 145° C. At eight hour intervals the inner screen area was cleaned by brushing off. The experiment was continued over a period of three weeks.

A product of 99.95% purity was recovered. A product, which still contained 24.32% by weight PMDA precipitated from the gases which passed the screen through further cooling off. The product amounts had a ratio of 1:0.21. Therefrom one can calculate a selectivity of the PMDA-sublimation in the sublimator of 94%.

Based on the findings of the above mentioned examples, the most varied sublimation apparatuses can be constructed. The apparatus illustrated in FIG. 3 can, for example, be constructed as follows:

A pipe 1.850 mm long and a diameter of 1.000 mm is provided with a cover at the upper end and a conical portion with a total height of 620 mm at the lower end. The bottom of the conical portion downward is formed by a cover of 410 mm in diameter. A ring of 60 mm width is soldered on at a height of 200 mm in the cylindrical part. Below this ring the gas feed connection is tangentially attached. The entire sheath of the apparatus below the above ring can be heated via soldered-on pipes (e.g. via steam). The heating of the lower cover takes place via IR-radiation. The sublimation basket rests on the above ring. It consists of a conical screen tin sheath, whose lower diameter corresponds with the ring opening, while the upper diameter is smaller by about 40%. At the upper edge of this truncated cone another truncated cone-like screen-tin-sheath is attached in such a manner that the smaller diameter points downward and tightly encloses a central pipe which reaches down from the upper cover. Cooling pipes, which are fed with warm oil, are affixed to the outer side of the larger and to the inner side of the smaller truncated cone sheath. The feed lines to the cooling pipes are for practical purposes guided through the cover. Also the entire sublimation basket is hung up on the cover. Below the cover the gas exit connection is affixed to the outer sheath of the apparatus. Cover and sheath above the soldered-in ring are heat insulated, however, they are not heated.

A shaft is placed through the above central pipe, which activates the wiper blade in the interior of the sublimation basket. This wiper blade is provided with a steel brush border at its edges.

A total screen area of about $5mm^2$ is contained in the apparatus of the above named measurements. It is sufficient for a throughput of about 100 $Nm^3$ of reaction gas/h or for a PMDA yield of about 0.5 tons/month.

What is claimed is:

1. An apparatus for the recovery of higher melting, organic materials comprising upright container means with gas inlet means laterally connected to the lower part of said container means, a gas outlet means connected to the upper part of the container means, at least one wall opposed to said gas inlet means and disposed in the path of gas flow from said gas inlet means to said gas outlet means, said wall defining a zone on the upstream side thereof and a zone on the downstream side thereof, said wall being perforated to permit gas to flow from said upstream side thereof to said downstream side thereof, said wall having attached thereto on the downstream side thereof cooling means comprising at least one thermostatically controlled cooling coil through which passes a cooling fluid, said apparatus having collection means for collecting solids deposited on the upstream side of said wall, said wall being at least partially opposed to a bottom portion of said apparatus and tapering downward with means for product removal.

2. Apparatus of claim 1 wherein the wall has the shape of a half hollow sphere, whereby the opening is facing toward the flow side.

3. Apparatus of claim 1 wherein the wall has the shape of a hollow cone or a hollow truncated cone, whereby the bottom area represents the opening which is facing the oncoming flow side.

4. Apparatus of claim 1 wherein the wall has the shape of a hollow pyramid or hollow truncated pyramid, whereby the bottom area represents the opening which is facing the oncoming flow side.

5. Apparatus of claim 1 wherein the wall has the shape of a hollow circular hollow bulge, whereby the opening is facing the oncoming flow side.

6. Apparatus of claim 1 wherein the wall has the shape of a hollow cylinder, the open bottom area of which is facing the oncoming flow side.

7. Apparatus of claim 1 wherein the wall represents a horizontal or inclined plane area.

* * * * *